United States Patent [19]

Ferguson et al.

[11] Patent Number: 5,026,635
[45] Date of Patent: Jun. 25, 1991

[54] STABLE HUMAN CELL LINES EXPRESSING AN INDICATOR GENE PRODUCT UNDER VIRUS-SPECIFIC GENETIC CONTROLS

[75] Inventors: Blair Q. Ferguson, Wilmington; Lee T. Bacheler, Newark; Stephen R. Petteway, Hockessin, all of Del.; Russell H. Neubauer, West Chester, Pa.

[73] Assignee: Du Pont Merck Pharmaceutical, Wilmington, Del.

[21] Appl. No.: 515,132

[22] Filed: Apr. 26, 1990

Related U.S. Application Data

[62] Division of Ser. No. 51,970, May 19, 1987.

[51] Int. Cl.[5] .................... C12Q 1/70; C12Q 1/68; C12Q 1/00; C12P 21/06

[52] U.S. Cl. ..................... 435/5; 435/6; 435/240; 435/243; 435/69.1; 435/32; 435/18; 435/26; 514/19; 530/350

[58] Field of Search ................. 435/5, 6, 7, 240, 243, 435/69.1; 530/350; 514/19

Primary Examiner—Robert A. Wax
Assistant Examiner—Bradley L. Sisson

[57] ABSTRACT

The invention relates to stable mammalian cells lines having integrated in their genome two heterologous DNA sequences, a first DNA sequence which expresses a trans-acting regulatory protein, and a second DNA sequence which expresses a desired protein, said second DNA sequence being linked to a target DNA regulatory control sequence which is responsive to the expressed trans-acting regulatory protein.

2 Claims, 6 Drawing Sheets

| DNA TRANSFECTED INTO HeLa CELLS | CAT ASSAY | | | |
|---|---|---|---|---|
| | % CONVERSION | ASSAY TIME (MIN) | VOL. LYSATE (μl) | RELATIVE CAT |
| CARRIER | 0 | 195 | 20 | 0 |
| SV-CAT | 0.72 | 30 | 2.5 | 76 |
| LTR-CAT | 0.28 | 195 | 20 | 1 |
| SV-TAT | 0 | 195 | 20 | 0 |
| LTR-CAT + SV-TAT | 30.2 | 30 | 2.5 | 5600 |

2B.

| PLASMID TRANSFECTED INTO HeLa CELLS | IL2 SECRETED (UNITS/ml/$10^6$ CELLS) |
|---|---|
| LTR-IL2 | < 0.01 |
| LTR-IL2 + SV-TAT | 5 |
| LTR-CAT | < 0.01 |
| LTR-CAT + SV-TAT | < 0.01 |

JURKAT 5 to 25 UNITS IL2/ml/$10^6$ CELLS
0.01 to 0.08 μg IL2/ml/$10^6$ CELLS

2C.

| DNA TRANSFECTED INTO HeLa CELLS | β-gal ASSAY | | | |
|---|---|---|---|---|
| | VOL. (μl) | TIME (MIN) | OD 420 | RELATIVE βgal |
| CARRIER | 10 | 180 | 0.013 | 1.6 |
| LTR-βgal | 10 | 180 | 0.010 | 1.2 |
| SV-TAT | 10 | 180 | 0.010 | 1.2 |
| LTR-βgal + SV-TAT | 10 | 10 | 0.797 | 1770 |

FIGURE 3

| CELL TYPE | GENE | CAT ACTIVITY | | |
|---|---|---|---|---|
| | | RELATIVE TO LTR-CAT | RELATIVE TO SV-CAT | RELATIVE TO SV-CAT IN HeLa |
| CHO (HAMSTER) | SV-CAT | 51 | 1.0 | 0.74 |
| | LTR-CAT | 1.0 | 0.020 | 0.015 |
| | LTR-CAT + SV-TAT | 23 | 0.44 | 0.33 |
| HeLa (HUMAN) | SV-CAT | 76 | 1.0 | 1.0 |
| | LTR-CAT | 1.0 | 0.013 | 0.013 |
| | LTR-CAT + SV-TAT | 4200 | 55 | 55 |
| 3T3 (MOUSE) | SV-CAT | 5.3 | 1.0 | 0.86 |
| | LTR-CAT | 1.0 | 0.19 | 0.16 |
| | LTR-CAT + SV-TAT | 10 | 1.9 | 1.6 |
| PK (PIG) | SV-CAT | 1.3 | 1.0 | 0.54 |
| | LTR-CAT | 1.0 | 0.79 | 0.42 |
| | LTR-CAT + SV-TAT | 3.6 | 5.2 | 2.8 |
| L (MOUSE) | SV-CAT | 21 | 1.0 | 0.16 |
| | LTR-CAT | 1.0 | 0.048 | 0.0077 |
| | LTR-CAT + SV-TAT | 7.6 | 0.37 | 0.059 |

FIGURE 4

| TRANSFECTED GENES | CLONE | IL2 SECRETED (UNITS/ml/$10^6$ CELLS) |
|---|---|---|
| SV-NEO | 10-POOL | 0 |
| SV-TAT | 2-14 | 0 |
| LTR-ßgal + SV-TAT | 12-8 | 0 |
| | 12-10 | 0 |
| | 12-11 | 0 |
| LTR-IL2 | 13-POOL | 0 |
| | 13-1 | 0 |
| | 13-3 | 0 |
| | 13-4 | 0 |
| | 13-7 | 0 |
| | 13-8 | 0 |
| | 13-10 | 0 |
| | 13-11 | 0 |
| | 13-12 | 0 |
| LTR-IL2 + SV-TAT | 14-POOL | 10 |
| | 14-1 | 0 |
| | 14-2 | 15 |
| | 14-3 | 2.5 |
| | 14-4 | 26 |
| | 14-5 | 0 |
| | 14-6 | 0.01 |
| | 14-7 | 15 |
| | 14-8 | 34 |
| | 14-9 | 0 |
| | 14-10 | 0.7 |
| | 14-11 | 0.01 |
| | 14-12 | 0.12 |
| | 14-13 | 0 |

JURKAT 5-25 UNITS IL2/ml/$10^6$ CELLS
.02-.08 µg IL2/ml/$10^6$ CELLS

FIGURE 5

| HeLa CLONE | RELATIVE β-gal | βgal FOLLOWING TRANSFECTION OF SV-TAT | TAT ACTIVITY: RELATIVE CAT FOLLOWING TRANSFECTION OF LTR-CAT |
|---|---|---|---|
| SV-NEO | | | |
| 10-POOL | 2.1 | 3.0 | 0.2 |
| 10-6 | 0 | 0 | 0.2 |
| | | | |
| SV-NEO + LTR-βgal | | | |
| 11-POOL | 2.9 | 112 | 0.2 |
| 11-1 | 0 | 0 | 0.3 |
| 11-3 | 9.5 | 1820 | |
| 11-4 | 0.86 | 59 | |
| 11-5 | 0 | 610 | |
| 11-6 | 4.3 | 3.0 | |
| 11-7 | 1.0 | 1.0 | |
| 11-9 | 1.4 | 0.5 | |
| 11-10 | 0.7 | 0.9 | |
| 11-11 | 4.1 | 4.1 | |
| | | | |
| SV-NEO + LTR-βgal + SV-TAT | | | |
| 12-pool | 753 | 759 | 20 |
| 12-6 | 207 | 213 | |
| 12-7 | 0.5 | 0.6 | |
| 12-8 | 1760 | | >98 |
| 12-10 | 1000 | 1080 | >98 |
| 12-11 | 0 | 0 | >98 |
| 12-13 | 65 | 98 | >98 |
| 12-17 | 14 | 18 | 8 |

STABLE HUMAN CELL LINES EXPRESSING AN INDICATOR GENE PRODUCT UNDER VIRUS-SPECIFIC GENETIC CONTROLS

This is a division of application Ser. No. 07/051,970, May 19, 1987.

FIELD OF INVENTION

The invention relates to the derivation by genetic engineering of stable mammalian cell lines that specifically express an easily assayable indicator protein (such as E. coli β-galactosidase) under the genetic control of a virus-specific (HIV-specific) regulatory DNA sequence (such as the HIV LTR) and regulatory protein (such as HIV gene product). The invention provides a system that allows efficient screening of a specific class of antiviral (anti-HIV) therapeutic compounds.

BACKGROUND

The human immunodeficiency virus-I (HIV-I, also LAV, HTLV-III, or ARV) is the primary etiologic agent of the acquired immune deficiency syndrome (AIDS) [Barre-Sinoussi et al., Science, 220:868–871 (1983); Gallo et al., Science 224:500–503 (1984); Levy et al., Science 225:840–842 (1984)]. In addition to the gag, pol and env genes that encode the major virus structural proteins, the genome of HIV contains several other open reading frames designated sor, tat, art/trs and 3'-orf which encode additional viral proteins. These proteins are known to serve important regulatory functions during the HIV infectious cycle.

As used herein, the term "gene" connotes the DNA sequence information that specifies the expression of a particular protein product.

As first described by Haseltine and Wong-Staal and their colleagues, one important regulatory protein, the product of the tat gene, mediates the activation of the expression of gene sequences linked to the HIV LTR promoter region [Sodroski et al., Science 227:272–173 (1985); Arya et al., Science 229:69–73 (1985); Sodrocski et al., Science 229:74–77 (1985)]. This positive control of gene expression by the tat protein is an example of a phenomenon termed trans-activation. Trans-activation refers to the positive regulation of the expression of a specific target gene by a specific regulatory protein.

Positive-acting regulatory proteins and corresponding responsive target genes are well known in both prokaryotic and eukaryotic cell systems, as well as in many viruses. For example, many other animal viruses, as in the case of HIV, encode trans-activator proteins that are known to positively regulate viral gene expression. These viruses includes herpes viruses (such as herpes simplex virus, cytomegalovirus), adenoviruses, papovaviruses (such as SV40, polyoma virus, JC virus), leukemia retroviruses (such as bovine leukemia virus, HTLV-I, HTLV-II) and other lentiviruses (such as visna virus, equine infectious anemia virus, simian immunodeficiency virus). In addition to positive-acting regulatory proteins, examples of endogenous cellular and viral negative-acting regulatory proteins are known that can negatively regulate, i.e., repress, the expression of specific target genes.

The sequence information within the HIV LTR that is responsive to trans-activation by tat residues between nucleotides -17 and +58 (numbering is relative to the transcription start site) [Rosen et al., Cell 41:813–823 (1985); Muesing et al., Cell 48:691–701 (1987)]. This trans-activation target sequence may be directly recognized by the tat protein. Activation of expression of LTR-linked sequence by tat involves can increase in mRNA accumulation [Cullen, Cell 46:973–982 (1986); Gendelman et al., Proc. Natl. Acad. Sci. 83:9759–9763 (1986); Wright et al., Science 234: 988–934 (1986); Peterlin et al., Proc. Natl. Acad. Sci. 83:9734–9738 (1986); Musing et al., Cell 48:691–701 (1987)] and possibly post-transcription regulation [Rosen et al., Nature 319:555–559 (1986); Cullen, Cell 46:973–982 (1986); Feinberg et al., Cell 46:807–817 (1986)].

The derivation of stable human cell lines containing integrated heterologous genes expressing functional HIV tat [Rosen et al., J. Virol. 57:379–384 (1986); Cullen, Cell 46:973–982 (1986)] or a gene containing the chloramphenicol acetyl transferase (CAT) coding sequence linked to a HIV LTR [Wright et al., Science 234:988–992 (1986)] has been previously reported. Wright et al. showed further that the integrated LTR-cat gene was inducible by a transiently introduced tat-expressing gene. However, no previous report describes the derivation of stable human cell lines containing both the tat-expressing gene and the LTR-linked indicator gene.

The tat gene product is known to be essential for HIV replication [Dayton et al., Cell 44:941–947 (1986); Fisher et al., Nature 320:367–371 (1986)]. It is of considerable interest to determine the molecular mechanism by which the tat gene product induces gene expression. Since tat is an essential and virus-specific component of the HIV life cycle, specific inhibitors of tat function are likely to be important anti-HIV viral therapeutic agents. The present invention provides a system that allows for rapid screening and identification of compounds that specifically interfere with HIV tat function. The ability to identify compounds that selectively attack a virus without harming its mammalian host, offers the potential for effective yet nontoxic anti-viral drugs.

Importantly, the system we describe for the identification of inhibitors of HIV lends itself to simple, semi-automated nonradioactive assays that are free of infectious HIV. Moreover, the experimental strategy and screening methodology demonstrated here for HIV could be applied to other viral and mammalian cell systems for the identification of inhibitors of other specific positive-acting or negative-acting regulators of gene expression. Thus, the system demonstrated here is not limited to the identification of anti-viral therapeutic agents and could be applied to the identification of therapeutic agents for other disease conditions.

SUMMARY OF THE INVENTION

The invention relates to the derivation of genetically engineered stable mammalian cell lines that contain integrated into the host genome two types of recombinant heterologous genes. The first gene expresses a protein capable of regulating the expression of the second gene. The second gene contains a target DNA regulatory sequence which is responsive to or recognized by the regulatory protein expressed by the first gene. The second gene encodes and expresses any gene product of particular interest. A detailed understanding of the molecular mechanism by which the regulatory protein affects gene expression from the responsive DNA sequence is not required.

In particular, stable human cell lines have been derived that contain integrated copies of two types of recombinant heterologous genes; one gene expresses the HIV tat gene product and the second gene contains a coding sequence, for example, an indicator protein coding sequence, linked to an HIV LTR sequence. For the expression of HIV tat protein, we have placed the HIV tat coding sequence under the control of transcription signals derived from the simian virus 40 (SV40) early region, to yield plasmid pSV-tat. LTR-linked indicator genes were constructed using coding sequences derived from bacterial chloramphenicol acetyl transferase (cat), *E. coli* β-galactosidase, and human IL2 (interleukin 2), to yield the plasmids pLTR-cat, pLTR-βgal, and pLTR-IL2, respectively. The HIV LTR is known to contain sequence information that is responsive to the tat protein and mediates the tat-dependent activation of expression of sequences that are linked to the LTR. Thus, the expression of the LTR-linked indicator gene product is dependent on and tightly controlled by the HIV tat gene product. Stable human HeLa-derived cell lines were isolated that express at relatively high levels either CAT, β-galactosidase or IL2 under the control of the HIV LTR and tat gene product. In the absence of functional tat, expression of β-galactosidase or IL2 directed by the HIV LTR is below the detection limit of our assays. CAT is expressed at very low levels from the HIV LTR in the absence of functional tat. Thus, the high level of expression of the indicator gene in these stable cell lines is dependent on the presence of functional tat protein. The ability to obtain stable cell lines constitutively expressing a given gene product requires that the gene product not be lethal to the host cell at the level that is expressed. It has, therefore, been established that relatively high level expression of CAT, IL2, or β-galactosidase is not lethal to HeLa cells.

DETAILED DESCRIPTION

Mammalian Cell Transfection, Growth and Selection

Figure 1:
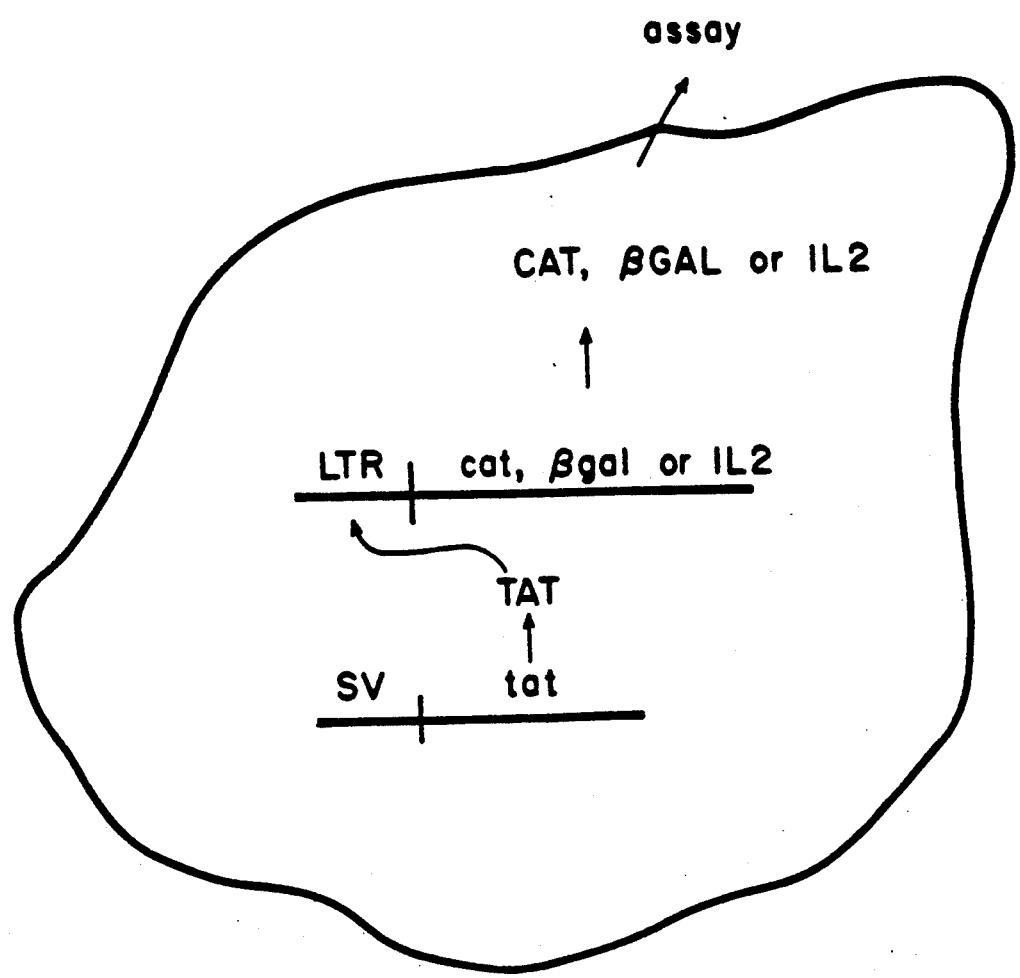

Mammalian cell lines were maintained as monolayer cultures in Dulbecco's modified minimal Eagle's medium (DMEM) with high glucose and supplemented with 10% calf serum (Hazleton Research Products, Denver, PA). Cells were plated at $5 \times 10^5$ cells per 60 mm tissue culture dish and were transfected the next day using the calcium phosphate co-precipitation procedure [Graham and Van der Eb, *Virology* 52:456-467 (1973); Wigler et al., *Proc. Natl. Acad. Sci.* 76:1373-1376 (1979)]. In transient studies the cells were harvested at 48 hours after transfection.

Stable mammalian cells containing integrated copies of transfected plasmid DNA were derived using the pSV2-neo dominant selectable marker and selection for resistance to the antibiotic G418 (Gibco Laboratories, Grand Island, NY) [Southern and Berg, *J. Mol. Appl., Genet.* 1:327-341 (1982); Colbere-Garapin et al., *J. Mol. Biol.* 150:1-4 (1981)]. Plasmid pSV2-neo was obtained from American Type Culture Collection, Rockville, MD. At 24 hours following transfection, cells in each 60 mm culture dish were split into three 100 mm culture dishes. At 48 hours following transfection, cells were placed in full medium containing G418 (600 μg/ml). After 10 to 14 days growth in selective medium, G418-selected colonies of cells were either pooled or isolated using cloning cylinders. Cells were maintained in G418-containing medium during continued growth.

Plasmid Construction

Plasmid constructions were carried out using standard methodology as described by Maniatis et al., *Molecular Cloning: A Laboratory Plasmid*, Cold Spring Harbor Laboratory, New York (1982), the teaching of which is hereby incorporated by reference. Enzymes and other reagents used for plasmid constructions were obtained from Bethesda Research Laboratories, Gaithersburg, MD or New England Biolabs, Beverly. MA. Methods for digesting, identifying, recovering, and purifying the various nucleotide sequences used in the invention are known to those skilled in the art as are methods for ligating the sequences into vectors, transforming host microorganism strains, cloning, and recovering products synthesized. Accordingly, the methods will only be described by reference to specific embodiments of the invention set forth hereinafter.

Plasmid pSV2-cat contains the bacterial chloramphenicol acetyl transferase (cat) coding sequence under the transcriptional control of the SV40 early promoter and polyadenylation signals [Gorman et al., *Mol. Cell. Biol.* 2:1044-1051 (1982)]. In plasmid pCH110 an *E. coli*-derived β-galactosidase coding sequence is similarly placed under SV40 early transcriptional control [Hall et al., *J. Mol. Appl. Genet.* 2:101-109 (1983)]. pSV2-cat and pCH110 were obtained from American Type Culture Collection and Pharmacia, Piscataway, NJ, respectively. We refer throughout to pSV2-cat and pCH110 as pSV-cat and pSV-βgal, respectively.

Plasmid p5'LTR-cat was derived from pSV-cat by replacing the 259 base pair PvuII to HindIII fragment containing the SV40 origin region with a 650 base pair HpaI to HindIII 5'LTR-containing DNA fragment from the biologically active proviral clone pHXB2gpt (obtained from A. Fisher, H1H, Bethesda, MD) [Fisher et al., *Nature* 320:367-371 (1986)]. Plasmid p3'-LTR-cat was constructed similarly using a 720 base pair XhoI to HindIII 3'LTR-containing DNA fragment from pHXB2gpt. The XhoI site was converted to a blunt end by Klenow reaction prior to ligation.

Plasmid pLTR-βgal was constructed by replacing the HindIII to BamHI fragment containing the cat coding sequence from p5'LTR-cat with the HindIII to BamHI βgal-containing segment from pSV-βgal.

Plasmid pSV-tat was derived from pSV-cat by replacing the HindIII to HpaI cat-containing fragment with a 2628 base pair SalI to BamHI fragment containing the HIV tat coding sequence from pHXB2gpt. Prior to ligation, the SalI site was converted to a HindIII site using a HindIII to SalI oligonucleotide linker and the BamHI site was converted to a blunt end by Klenow reaction.

Plasmid pLTR-IL2 was derived from p3'LTR-cat by replacing the HindIII to HpaI cat-containing segment with a 400 base pair RsaI to StuI fragment containing the human IL2 coding sequence from plasmid pY3. Plasmid pY3 contains a human IL2 cDNA and was obtained from K. Livak (Du Pont Experimental Station, Wilmington, Del.). The IL2 coding sequence in pY3 is identical to that reported by Taniguchi et al., *Nature* 302:305-310 (1983).

Chloramphenicol acetyltransferase and β-galactosidase assays

Cells were lifted from 60 mm culture plates using 1 mM EDTA in PBS, pelleted, and either stored at −70° C. or assayed immediately. Cell lysates were prepared by suspension of the cell pellet in 50 μl containing 250 mM sucrose, 10 mM Tris-HCl (pH 7.4), 10 mM EDTA, followed by three repetitive freeze and thaw cycles, and removal of cell debris by centrifugation. Cell lysates were assayed for chloramphenicol acetyltransferase (CAT) activity according to Gorman et al., *Mol Cell. Biol.* 2:1044–1051 (1982). The conversion of chloramphenicol to the acetylated forms was quantitated by silica gel thin-layer chromatography and liquid scintillation counting of spots removed from the plate.

β-galactosidase assays were performed as described (Pharmacia Analects Newsletter, vol. 14, No. 2). For the determination of the relative CAT or β-galactosidase activity initial reaction rates were measured (i.e., the formation of product was proportional to the volume of cell extract assayed and the assay incubation time) and each assay was normalized for the volume of cell extract used and the assay incubation time.

IL2 Assay

Cell culture medium was assayed directly for secreted IL2 and was performed using the IL2-dependent murine cell line CTLL as described [Robb, *Meth. Enzymol.* 116:493–525 (1985)]. Purified human Jurkat cell-derived IL2 has a specific activity of approximately 300 units per µg using the assays performed here (L. Breth, Du Pont Glasgow Site, Glasgow, Del.).

FIGURE LEGENDS

FIG. 1: Schematic representation of the system used to demonstrate trans-activation of the HIV LTR by the HIV tat gene product. Two types of heterologous genes are transferred into the human cell; one gene (SV-tat) expresses the HIV tat gene product (TAT) and the second gene contains an indicator protein coding sequence linked to the HIV LTR (LTR-cat, LTR-βgal, or LTR-IL2). Following gene transfer, expression of the indicator gene product (CAT, βgal, or IL2) is quantitated.

FIG. 2: HIV tat-dependent induction of expression of indicator genes linked to an HIV LTR in transient expression assays. HeLa cells were transfected with the indicated plasmids and cell lysates were prepared at 48 hours following gene transfer. Transfections contain a total of 10 to 15 µg of DNA per 60 mm culture plate using sonicated salmon sperm DNA as carrier. The amounts of plasmid DNA used in each transfection are given as follows: A) 3 µg pSV-cat or pLTR-cat, 5 µg pSV-tat, and 10 µg total DNA; B) 5 µg pLTR-IL2, 10 µg, pSV-tat, and 15 µg total DNA; C) 5 µg pLTR-βgal, 10 µg pSV-tat, and 15 µg total DNA.

FIG. 3: HIV tat-dependent induction of expression of CAT from pLTR-cat in transient assays in cell types from different species. Mammalian cells were transfected with the indicated plasmids and cell lysates were prepared at 48 hours following gene transfer. Transfections contained a total of 7 µg of DNA per 60 mm culture plate using sonicated salmon sperm DNA as carrier. The amounts of plasmid DNA used in each transfection are given as follows: 2 µg pSV-cat, 2 µg pLTR-cat, and 5 µg pSV-tat. The CAT activity in transfected cell lysates was quantitated and normalized either to the level of CAT expressed in cells of the same type transfected with pLTR-cat or pSV-cat, or the level of CAT expressed in HeLa cells transfected with pSV-cat. The source of the cell lines used is given as follows: NIH3T3, CHO, and HeLa (American Type Culture Collection); PK (M. Whealy, Du Pont Experimental Station, Wilmington, Del.); L (M. Linn, Du Pont Experimental Station, Wilmington, Del.).

FIG. 4: Derivation of stable human cell lines expressing functional secreted IL2 under the control of the HIV LTR and HIV tat gene product. HeLa cells were transfected with the indicated plasmids (0.5 µg pSV-neo, 5 µg pLTR-IL2, 10 µg pSV-tat, 16 µg total DNA per 50 mm culture plate) and selected for growth in G418. G418-selected colonies of cells were either pooled or cloned individually and subsequently assayed for secreted IL2.

FIG. 5: Derivation of stable HeLa cell lines expressing functional β-galactosidase under the control of the HIV LTR and HIV tat gene product. HeLa cells were transfected with the indicated plasmids (0.5 µg pSV-neo, 5 µg pLTR-βgal, 15 µg pSV-tat, 16 µg total DNA per 60 mm culture plate) and selected for growth in the presence of G418. G418-selected colonies of cells were pooled and cloned individually and subsequently assayed for β-galactosidase (second column). Some of the pooled or cloned G418-selected cells were analyzed for tat-inducible β-galactosidase, i.e., a tat-inducible LTR-β-gal gene, by transient introduction of the tat-expressing pSV-tat plasmid. At 48 hours following gene transfer of pSV-tat, the cells were assayed for β-galactosidase activity (third column). Some of the pooled or cloned G418-selected cells were analyzed for the expression of functional tat gene product by transiently introducing the pLTR-cat indicator gene. At 48 hours following gene transfer of pLTR-cat, cells were assayed for CAT activity (fourth column). Tat activity is expressed in arbitrary units corresponding to the level of expression of CAT from pLTR-cat.

Figure 6:
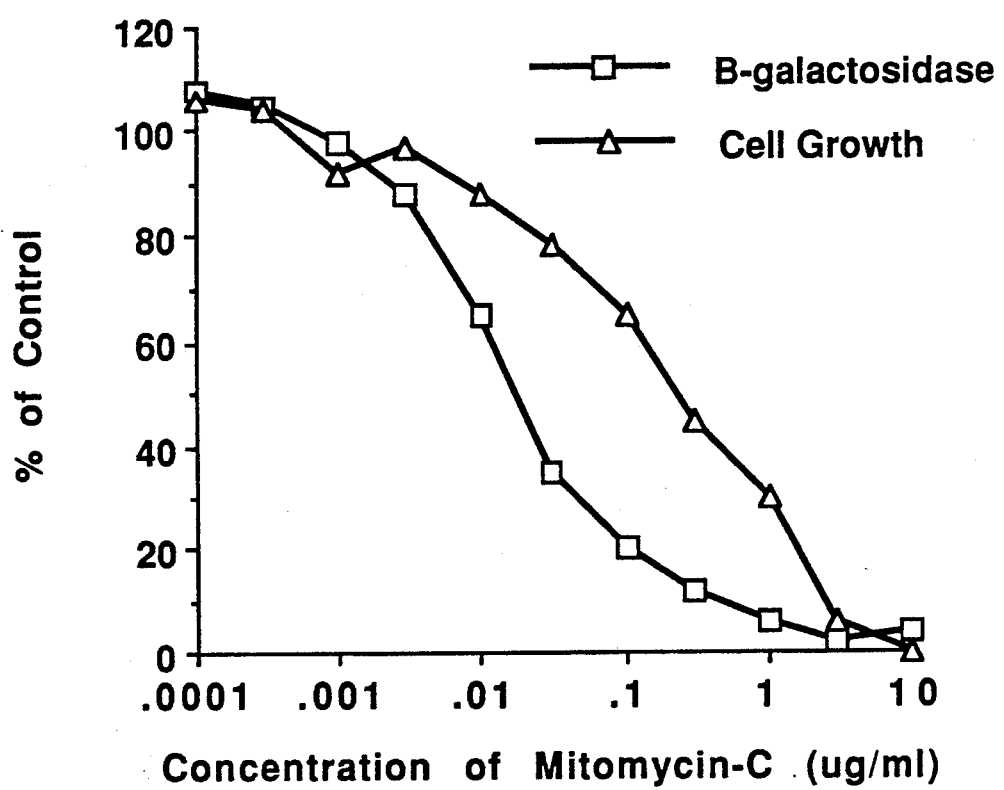

FIG. 6: Effect of mitomycin-C on the growth and β-galactosidase expression of 12-8 cells. HeLa-derived clone 12-8 cells (see FIG. 5) were seeded at $5 \times 10^3$ cells per well in a 96-well microtiter plate. At one day following seeding, the culture medium was replacing with medium containing varying concentrations of mitoycin-C. At four days following seeding, cell growth and β-galactosidase were assayed.

EXAMPLE 1

Demonstrated of tat-mediated Trans-activation of LTR-Linked Gene Expression in Transient Assays The ability of the tat gene product expressed from pSV-tat to trans-active expression of LTR-linked cat, β-galactosidase, and IL2 was analyzed by transient transfection and expression assay. These arrays involve gene transfer or transfection of different combinations of plasmids into HeLa cells and quantitating the level of indicator gene product expressed at 48 hours following gene transfer. Under the conditions used, approximately 5% of the target cells are expected to take up and functionally express genes present in the transfected plasmid DNA. However, the transfected and expressed DNA is not necessarily stably integrated into the host genome. Indeed, the frequency of stable integration and expression of transfected DNA is considerably lower—approximately 0.1% of the target HeLa cells. Thus, the assay of gene expression at 48 hours following gene transfer is referred to as a transient expression assay.

The results of such transient transfection and expression assays are given in FIG. 2. For pLTR-cat, the tat-dependent induction of cat expression is approximately 5600-fold. The CAT assay is sufficiently sensitive to permit the detection of CAT from the non-induced LTR-cat gene. In the case of pLTR-IL2 and pLTR-βgal, the non-induced level of expression of IL2 or β-galactosidase is below the limit of detection. In the presence of tat, significantly increased levels of IL2 and β-galactosidase are expressed from pLTR-IL2 and pLTR-βgal, respectively. The tat-dependent induction of LTR-IL2 and LTR-βgal in HeLa cells is determined to be greater than 500-fold or 1770-fold, respectively.

EXAMPLE 2

Species Specifically of HIV tat and LTR-mediated Transactivation

Since one of our goals in studying tat-mediated expression of HIV LTR-linked genes was to evaluate this activator and promotor combination as a general tool for the high level expression of heterologous proteins in mammalian cells, we examined both the absolute level of expression, and the degree of trans-activation by the tat gene product in a variety of fibroblast-like cells from different species. For this analysis, transient transfection and expression assays were performed. The results are given in FIG. 3. Surprisingly, we found that tat-mediated trans-activation of the HIV LTR was considerably more efficient in the human cell line tested (HeLa) as compared with each of the non-human cell lines tested. Thus, whereas the tat-dependent fold induction of cat expression in HeLa cells in the experiment shown was 4200-fold, the hold induction in the non-human cells was only 3.6 to 23-fold. It appears that a major component of the trans-activation exhibited by the HIV tat gene product is species specific.

The level of gene expression in HeLa cells directed by the HIV tat-activated LTR was approximately 55-fold greater than the level seen with the SV40 early promoter. Thus, the HIV tat and LTR-mediated expression system appears to be a useful tool for the expression at relatively high level of inserted gene sequences. This system may be of considerable value as a means for producing useful polypeptides, as for example, IL2. However, the major utility of the HIV tat and LTR-mediated expression system appears to be limited to a human cell host. It is likely, however, that analogous trans-activator-containing expression systems may be stably integrated into other mammalian cell lines. Since a major component of tat function appears to be human specific, we derived stable cell lines exhibiting tat function using a human cell host (i.e., HeLa cells).

EXAMPLE 3

Derivation of Stable Human Cell Lines Exhibiting HIV tat Function

For studies of the molecular mechanism of tat activation and for further evaluation of the utility of tat-mediated expression for the stable expression of heterologous proteins in human cells, we wanted to derive stable transfected cell lines which contained either a functional tat gene alone, an LTR-indicator gene in a form capable of being activated by the tat protein, or both the tat- and LTR-containing genes. In particular, stable cell lines expressing an easily assayable indicator gene product under tat and LTR control would be useful as target cells for screening of inhibitors of tat function.

For the derivation of stable cell lines the pSV2-neo dominant selectable marker was used. Expression of the neo gene confers resistance to the drug G418. In practice there is a high probability that transfected cells that stably express pSV2-neo DNA will also express genes that are co-transfected with the pSV2-neo plasmid. We therefore transfected various combinations of our tat-containing and LTR-containing plasmid constructions with pSV2-neo into HeLa cells and selected for cells that were resistant to G418. G418-selected colonies of cells were subsequently pooled or cloned and analyzed for expression of functional tat and/or tat-dependent expression of the LTR-linked indicator gene.

Using this protocol, we have isolated HeLa-derived cell lines that express functional tat gene product (in the absence of a LTR-linked indicator gene). For example, see HeLa-derived clone 12-11, FIG. 5. Stable cell lines containing either pLTR-cat or pLTR-βgal in a tat-inducible state were also isolated. For example, see HeLa-derived clones 11-13, 11-4 and 11-5, FIG. 5. In addition, we have isolated stable HeLa-derived cell lines that express either CAT, IL2, or β-galactosidase at relatively high levels under the control of the HIV LTR and tat gene product. For example, HeLa-derived clones 14-8 (FIG. 4) and 12-8 (FIG. 5) express relatively high levels of IL2 and β-galactosidase, respectively. A subclone of clone 12-8 has been isolated and is designated B-9.

In a similar manner, we have also isolated HeLa-derived cell clones that contain pSV-βgal and constitutively express detectable levels of β-galactosidase. One such HeLa-derived clone is designated 8-10. Since the expression of β-galactosidase in clone 8-10 is independent of HIV tat, these cells are a particularly useful component of a tat-inhibitor screening protocol as a target to test the specificity of any potential inhibitor for HIV tat. Thus, compounds which inhibit the tat-dependent β-galactosidase expression in HeLa-derived clone 12-8 or B-9, without affecting the tat-independent β-galactosidase expression in clone 8-10, are potentially specific inhibitors of tat function.

HeLa derived clones B-9 and 8-10, as described in Example 3, have been deposited with the American Type Culture Collection, Rockville, MD and bear deposit accession number CRL9432 and CRL9423, respectively. These deposits are available to the public upon the grant of a patent to the assignee. However, it should be understood that the availability of a deposit does not constitute a license to practice the subject manner in derogation of patent rights granted by governmental action.

The derivation of stable cell lines which exhibit high level expression of an easily assayed indicator gene product under the control of the HIV tat gene, should have considerable utility in further studies of the mechanism of action of the tat gene product, and in drug discovery studies designed to identify compounds with interfere with tat-mediated LTR-driven gene expression. Mutations in the HIV tat gene can be readily screened for biological activity by transfection into cell lines containing activatable LTR-cat or LTR-βgal. These assays can be performed in the absence of infectious virus, and are highly sensitive, particularly if CAT is used as a indicator gene, as well as rapid, inexpensive, and non-radioactive if β-galactosidase is chosen as the indicator gene. Experiments using such tat-activatable integrated LTR gene constructs closely mimic the integrated HIV provirus LTR that is the target for trans-activation by tat during the HIV infectious life cycle. During the HIV life cycle, trans-activation of the integrated provirus LTR results in the increased expression of viral genes and concomitant production of infectious virus.

EXAMPLE 4

Measurement of Cell Growth and β-galactosidase in 96-well Microtiter Plates

Cell lines such as HeLa-derived clone 12-8 or 12-10 (see FIG. 5) which express high levels of an easily detected indicator gene product under tight control and dependent on the activity of the HIV tat gene product may by very useful in the identification of compounds which interfere with tat activation. In an effort to facilitate the screening of large numbers of compounds, we sought to develop a semi-automated micro assay for the quantitation of β-galactosidase expression. For the detection of β-galactosidase expression in cells grown in a 96-well microtiter plate, we first used an indirect, immunological, enzyme-linked immunosorbant assay (ELISA). However, this method was not sufficiently sensitive to allow the detection of β-galactosidase in clone 12-6 (B-9) cells grown in a microtiter plate well. Unexpectedly, a direct β-galactosidase enzyme assay proved to be a very sensitive method for the quantitation of β-galactosidase expression in clone 12-8 (B-9) cells grown in a micro well (see below).

In parallel with the β-galactosidase assay, cell viability can also be monitored using a microtiter plate format (see below). It is desirable to monitor in parallel both the β-galactosidase expression and cell growth in response to a compound being tested, as a first check of the specificity of an inhibitor for tat. As discussed in Example 3, a second check for the specifically of an inhibitor for tat involves testing the effect of an inhibitor on β-galactosidase expression in a cell line, such as 8-10, where the expression of β-galactosidase is independent of tat function. Thus, a standard screening protocol for inhibitors of tat function involves quantitating the dose-dependent effect of a compound on cell growth and β-galactosidase, using both the HeLa-derived clones B-9 (tat-dependent β-galactosidase expression) and (8-10/tat-independent β-galactosidase expression).

The procedure used for the quantitation of cell growth and β-galactosidase expression is given below. Cells are seeded onto a 96-well microtiter plate in 0.1 ml medium per micro well. At 1 day following seeding of the cells, a compound to be tested may be added to the medium. After 4 days of growth, replicate plates are assayed for either cell number or β-galactosidase activity.

The number of viable cells in the micro well is determined colorimetrically following the addition of the yellow tetrazolium salt MIT (dimethylthiazole tetrazolium bromide). MIT is added to the cell culture medium (50 μul of 1 mg/ml MIT in $H_2O$ per 0.1 ml culture medium per micro well). Following incubation of the cells of 4 hours at 37° C., 0.1 ml of 0.04 N HCl in isopropanol is added to each micro well and the contents are mixed by pipetting. The optical density at 570 nm of the mixture is read using a microtiter plate reader (Biotech), within 15 minutes to 1 hour following addition of the acid isopropanol. Dehydrogenases, functional only in the viable cells, convert the yellow MIT to a purple formazan which is then solubilized for spectrophotometric measurement of optical density. Thus, the number of viable cells is proportional to the concentration (optical density) of the MIT reaction product formazan.

β-galactosidase activity is quantitated in the 96-well microtiter plate format using the following protocol. The medium is removed from the HeLa-derived cell monolayer and to each well is added 50 μl containing 250 mM sucrose, 10 mM Tris-HCl (pH7.4) and 10 mM EDTA. The cells are lysed by three repetitive freeze and thaw cycles. To each microwell is added 150 μl of buffer Z (60 mM $Na_2PO_4$, 40 mM $NaH_2PO_4$, 10 mM KCl, 1 mM $MgSO_4$, 50 mM β-mercaptoethanol, pH 7.0). The β-galactosidase reaction is initiated by the addition of 40 μl containing 4 mg/ml ONPG in buffer Z and indicated at 37° C. for 10 minutes to 4 hours. The formation of product is monitored by measuring the optical density at 415 nm using a microtiter plate reader. Other more sensitive substrates for β-galactosidase may be used. For both the cell number assay and β-galactosidase assay, data manipulation and analysis are via interface to a computer with customized software.

The effect of seeding density on growth and β-galactosidase expression of HeLa-derived clone 12-8 in micro wells on a 96-well microtiter plate was tested. The optimum seeding density for clone 12-8 is approximately $5 \times 10^3$ cells per micro well. The effect of the cytocidal drug mitomycin-C on the growth and β-galactosidase expression of 12-8 cells was examined as a preliminary test of the response of the system to a drug known to inhibit mammalian cell DNA replication and growth. As shown (FIG. 6), a clear dose-response effect of mitomycin-C on 12-8 cell growth and β-galactosidase expression was observed.

The development of the semi-automated procedures described for the rapid quantitation of cell number and β-galactosidase expression, greatly facilitates the application of this test system to large numbers of compounds in a screen for inhibitors of tat function. The cell lines described provide a target for identifying compounds that may specifically interfere with HIV tat function, as opposed to other essential HIV functions. Thus, compounds that are shown to interfere with the replication of infectious HIV could be tested in our HIV tat and LTR-indicator gene-containing cell lines to assess whether the mode of action of these compounds involves the inhibition tat function. The assays described are rapid, quantitative, inexpensive, and eliminate the constraints imposed by working with infectious HIV itself.

What is claimed is:

1. A method of identifying an agent which specifically inhibits the function of human immunodeficiency virus (HIV) TAT protein, comprising:
    (a) exposing a stable genetically engineered human cell line to a potential inhibiting agent, said cell line stably expressing HIV TAT protein and stably expressing *E. coli* β-galactosodase under the control of a fully TAT-induced HIV LTR; and
    (b) measuring a decrease in the expression of the β-galactosidase by the cell line following exposure to the potential inhibiting agent.

2. A method of identifying an agent which specifically inhibits the function of human immunodeficiency virus (HIV) TAT protein, comprising:
    (a) exposing a stable genetically engineered human cell line to a potential inhibiting agent, said cell line stably expressing HIV TAT protein and stably expressing human IL-2 under the control of a fully TAT-induced HIV LTR; and
    (b) measuring a decrease in the expression of the IL-2 by the cell line following exposure to the potential inhibiting agent.

* * * * *